United States Patent [19]
Dees

[11] Patent Number: 5,958,740
[45] Date of Patent: Sep. 28, 1999

[54] **GENETICALLY ENHANCED CELLULASE PRODUCTION IN *PSEUDOMONAS CELLULOSA* USING RECOMBINANT DNA TECHNOLOGY**

[75] Inventor: H. Craig Dees, Knoxville, Tenn.

[73] Assignee: Lockheed Martin Energy Research Corp., Oak Ridge, Tenn.

[21] Appl. No.: 08/934,883

[22] Filed: Sep. 22, 1997

[51] Int. Cl.⁶ .............................. C12P 19/14; C12N 9/42
[52] U.S. Cl. .................. 435/99; 435/209; 435/252.34; 435/262; 435/263; 424/94.61
[58] Field of Search ........................... 435/209, 232.34, 435/262, 263, 99; 424/94.61

[56] References Cited

U.S. PATENT DOCUMENTS

| | | | |
|---|---|---|---|
| 4,755,464 | 7/1988 | MacPhee et al. | 435/68 |
| 5,204,260 | 4/1993 | Ahmad et al. | 435/254 |
| 5,702,940 | 12/1997 | Dees | 435/252.1 |

OTHER PUBLICATIONS

Svheirlinck, T. et al. "Cloning and expression of cellulase and xylanase genes in *Lactobacillus plantarum*." Applied Microbiology and Biotechnology (1990), vol. 33, pp. 534–541.

Lejeune, A. et al. "Cloning of an endoglucanase gene from *Pseudomonas fluorescens* var. cellulosa into *Escherichia coli* and *Pseudomonas fluorescens*" Journal of Industrial Microbiology (Jun. 1986), vol. 1, No. 2, pp. 79–86.

*Primary Examiner*—Robert A. Wax
*Attorney, Agent, or Firm*—Quarles & Brady LLP

[57] ABSTRACT

An enhanced strain of *Pseudomonas celllulosa* was obtained by introducing a recombinant genetic construct comprising a heterologous cellulase gene operably connected to a promoter into ATCC 55702, mutagenizing the transformants by treatment with MNNG, and selecting a high cellulase producing transformant. The transformant, designated *Pseudomonas cellulosa* ATCC XXXX, exhibits enhanced levels of cellulase production relative to the untransformed *Pseudomonas cellulosa* strain #142 ATCC 55702.

5 Claims, No Drawings

GENETICALLY ENHANCED CELLULASE PRODUCTION IN *PSEUDOMONAS CELLULOSA* USING RECOMBINANT DNA TECHNOLOGY

STATEMENT REGARDING FEDERALLY SPONSORED RESEARCH OR DEVELOPMENT

This invention was made with government support under contract DE-AC05-96OR22464, awarded by the United States Department of Energy to Lockheed Martin Energy Research Corporation, and the United States Government has certain rights in this invention.

CROSS-REFERENCE TO RELATED APPLICATIONS

Not applicable.

BACKGROUND TO THE INVENTION

Space in industrial and domestic landfills is becoming increasingly scarce. In recent years, there has been a growing awareness that there is a need to conserve space in the existing landfills by reducing the volume of solid waste materials through a variety of means (e.g., recycling, reducing consumption, incineration, or other means).

Waste disposable cellulosic materials (e.g., newsprints, disposable diapers, shopping bags, fast food containers) contribute significantly to the total volume of waste in domestic landfills in the United States. Cellulosic materials are generally defined as those materials that contain cellulose, a polymer of β-D-glucose units. Environmental concerns have prompted major international food suppliers to replace styrofoam packaging materials with cellulosic packaging materials. This has resulted in a large new source of cellulosic waste deposited in the landfills.

There is intense interest in the biomass conversion of waste cellulosic products into alternative fuels. The availability of a commercially feasible means of converting cellulosic materials into a usable energy source would reduce the volume of solid waste deposited in landfills and reduce our dependence on foreign fossil fuels.

To date, efforts directed toward developing means for degrading cellulosic materials using microorganisms have focused on cellulose degrading fungi (e.g., *Trichoderma reesei*). However, there are disadvantages to working with fungi. Relative to bacteria, fungi are generally difficult to grow in a fermentor. Fungi are relatively difficult to manipulate by means of genetic engineering; therefore, the potential for enhancement of the cellulose degrading properties of a fungus by means of recombinant DNA technology is low. The use of cellulase-producing fungi in fermentations requires the addition of enzymes to prevent product inhibition of cellulase production, which increases the cost of using the technology.

As a consequence of the disadvantages of working with fungi, scientists in the field began to focus attention on employing bacterial strains in the degradation of cellulosic materials. Most of the efforts have concentrated on anaerobic cellulose-degrading bacteria. However, conducting fermentation reactions in the absence of oxygen is a difficult and expensive procedure, relative to aerobic fermentation.

In general, the bacterial and fungal species that have been employed in the degradation of cellulosic materials do not efficiently excrete cellulase into the surrounding growth medium or the cellulase produced cannot efficiently degrade solid cellulosic materials. As a consequence, chemical modification of cellulosic waste is often required to make the solid cellulosic materials available for biodegradation. This additional step increases the cost of the method, and reduces the environmental advantages to be gained through biodegradation of cellulosic materials.

Another problem that has been encountered in the art is that most cellulase-producing organisms produce cellulase under acidic conditions. Under acidic conditions, the cellulase tends to adhere to filtration membranes, making it difficult to recover the cellulase.

The situations in which cellulose-degrading microorganisms may be used to advantage are commonly associated with conditions that are unfavorable to the growth of most microorganisms. For example, cellulosic waste streams, paper production processes, and fossil fuel often produce extremely harsh environmental conditions. Bioreactor solid matrices are formed under severe conditions, for example, at a very alkaline pH.

Cellulosic waste streams and fossil fuels often contain hazardous materials in addition to the cellulosic products. The cost of bioremediation of waste streams and fossil fuels increases when multiple organisms must be added to the site in order to accomplish disparate goals.

What is needed in the art is a cellulase-producing bacterial strain that is able to tolerate harsh environmental conditions, including alkaline conditions, and which has been genetically engineered through recombinant: DNA technology to produce enhanced levels of cellulase, relative to the unmodified strain.

BRIEF SUMMARY OF THE INVENTION

It is an object of the present invention to provide a genetically engineered bacterial strain that is capable of producing extracellular cellulase at increased levels.

It is an object of the present invention to provide an efficient, economical method for degrading waste cellulose, coal, and other cellulosic materials.

The present invention is a bacterial strain having the characteristics of *Pseudomonas cellulosa* mutant strain ATCC 202032 comprising in its genome a recombinant vector having a heterologous cellulase gene and a selectable marker.

The present invention is a method for degrading cellulosic material comprising contacting the cellulosic material with an effective amount of a cellulase produced by a bacterial strain having the characteristics of *Pseudomonas cellulosa* mutant strain ATCC 202032 comprising within its genome a recombinant vector having a heterologous cellulase gene operably connected to a promoter, and a selectable marker.

DETAILED DESCRIPTION OF THE INVENTION

One aspect of the present invention is a high cellulase producing bacterial strain having the characteristics of *Pseudomonas cellulosa* mutant strain ATCC 202032 comprising within its genome a recombinant genetic construct comprising a heterologous cellulase gene that is operably connected to a promoter, and a selectable marker.

*Pseudomonas cellulosa* mutant strain ATCC 202032 is characterized by enhanced cellulase production relative to the high cellulase producing strain *Pseudomonas cellulosa* mutant strain 142 (ATCC 55702). *Pseudomonas cellulosa* mutant strain ATCC 202032 was obtained as described in detail in the examples below. Briefly, a recombinant genetic construct was introduced into *Pseudomonas cellulosa* mutant strain 142 (ATCC 55702), transformants were mutagenized by treatment with N-methyl-N'-nitrosoguanidine (MNNG), and high cellulase producing mutants were selected by a screening test, described below. The genetic construct comprises a vector that is able to replicate in *Pseudomonas cellulosa* mutant strain 142 (ATCC 55702), a heterologous cellulase gene that is operably connected to a promoter, and a selectable marker.

By "enhanced cellulase production" it is meant the production of an amount of cellulase activity that is significantly higher than that produced by ATCC 55702. Preferably, a bacterial strain having the characteristics of *Pseudomonas cellulosa* mutant strain ATCC 202032 produces at least about 3 times more cellulase than ATCC 55702. Most preferably, the mutant strain produces 7 times, or even as much as 10 times more cellulase than ATCC 55702.

*Pseudomonas cellulosa* mutant strain 142 (ATCC 55702) was derived from a cellulase-producing bacterium that was isolated from soil in the 1950's and placed in the National Council for Industrial Bacteriology repository in Scotland with the designation NCIB 10462. NCIB 10462, also known as *Pseudomonas cellulosa* #28, was deposited with the American Type Culture Collection and given Accession No. 55703. The taxonomic classification of ATCC 55702 and 55703 has not been definitively established, despite the extensive characterization described in the examples below. However, the organisms will be referred to herein as *Piseudomonas cellulosa* isolates or strains.

*Pseudomonas cellulosa* strain 142 (ATCC 55702) was obtained through mutagenesis of ATCC 55703 by MNNG treatment (Miller, *Experiments in Molecular Genetics*, pp 125–129, 1972). Characteristics of bacterial isolate *Pseudomonas cellulosa* 142 (ATCC 55702) that make this bacterium a suitable cloning host in the practice of the present invention include: (1) improved soluble cellulase production; (2) rapid degradation of solid cellulose and waste products; (3) UV sensitivity; (4) enhanced β-glucosidase activity; (5) tetracycline and ampicillin sensitivity; and (6) high levels of total carbohydrate production from solid cellulose. Bacterial isolate *Pseudomonas cellulosa* 142 (ATCC 55702) is further characterized by the ability to produce a cellulase having an operating pH range from about 5 to 11, enhanced production of extracellular cellulases (endoglucanases), and efficient cellulase production at low temperatures (20–24° C.).

The construction of a suitable recombinant vector comprising an heterologous cellulase gene and a selectable marker is described in the examples below. The recombinant vector is capable of being stably maintained in the target host, has several well-defined, unique restriction sites located external to essential sequences, a heterologous cellulase gene operably connected to a promoter functional in the target host, and a β-lactamase gene that confers resistance to ampicillin. The present invention is intended to encompass a recombinant vector having minor additions, deletions, or substitutions of sequences in the recombinant construct disclosed herein. For example, a recombinant vector in which the ampicillin marker is replaced with another selectable marker that confers resistance to an antibiotic to which untransformed host cells are sensitive would be within the scope of the invention. It is anticipated that the recombinant vector can be further manipulated to encode other desirable proteins (e.g., an enzyme useful in the production of fuel).

As described in the examples below, *Pseudomonas cellulosa* ATCC 202032 comprises in its genome a recombinant genetic construct having a cellulase gene that was derived from a strain of *Pseudomonas cellulosa*. It is anticipated that a bacterial isolate having the characteristics of *Pseudomonas cellulose* ATCC 202032 could be obtained by transformation of *Pseudomonas cellulosa* mutant strain 142 (ATCC 55702) with a recombinant genetic construct comprising any cellulase gene that is operably connected to a promoter. The cellulase gene may be a gene from *Pseudomonas cellulose* that is distinct from that described in the examples, or it may be a cellulase gene from any other species.

The recombinant genetic construct of the present invention was introduced into *Pseudomonas cellulosa* ATCC 55702 by means of electroporation. Other transformation methods known to the art could be used to transform the bacteria; the mode of introducing the gene into the bacteria is not of particular importance to the practice of the present invention.

Mutagenized transformants of *Pseudomonas cellulosa* ATCC 55702 containing the recombinant vector were selected on the basis of ampicillin resistance and increased production of extracellular cellulase relative to untransformed isolates of *Pseudomonas cellulosa* ATCC 55702.

A sample of a high cellulase producing genetically engineered strain of *Pseudomonas cellulosa* comprising in its genome the recombinant genetic construct described in the examples below was deposited with the American Type Culture Collection, Rockville, Md. under the conditions of the Budapest treaty, and assigned Accession Number 202032. Deposit of these samples does not imply or grant a license to use the bacterial mutant.

One wishing to practice the present invention could obtain ATCC 202032 through the ATCC. Alternatively, one could isolate the recombinant vector from a culture of ATCC 202032, use the isolated DNA to transform a bacterial isolate having the characteristics of *Pseudomonas cellulosa* 142 (ATCC 55702), mutagenize transformants, and select a high cellulase producing strain. Optionally, one could construct the recombinant vector according to the methods described below, use the vector to transform a bacterial isolate having the characteristics of *Pseudomonas cellulosa* 142 (ATCC 55702), mutagenize transformants, and select a high cellulase producing strain.

The present invention is also a method for degrading cellulosic materials comprising contacting the cellulosic material with an effective amount of a cellulase produced by a bacterial strain having the characteristics of *Pseudomonas cellulosa* ATCC 202032 comprising within its genome a recombinant genetic construct that can be stably maintained in, a cellulase gene that is operably connected to a heterologous promoter, and a selectable marker.

Characterization of ATCC 55702 and ATCC 55703

The metabolic and physical properties of ATCC 55703 and ATCC 55702 were examined utilizing a wide variety of standard bacteriological methods which included assimilation studies, fatty acid analysis, and lipid analysis.

ATCC 55703 and ATCC 55702 were maintained on solid media consisting of M9 liquid medium to which 15 grams per liter agarose had been added along with 0.1% carboxymethyl cellulose (CMC) as the sole carbon source. ATCC 55703 and ATCC 55702 were then transferred to trypticase soy agar prior to MIDI analysis. Fatty acid analysis by the MIDI system was performed on ATCC 55703 and ATCC 55702 growing anaerobically on 5% sheeps blood agar.

All studies to determine optimal pH and temperature for growth were performed in tryptic soy broth (TSB). Solid cellulosic media was prepared using a base of M9 salt solution to which was added a soluble cellulosic component (i.e., carboxymethyl cellulose (CMC)) (0.1% (w/v)) and agar (1.5% w/v). Cellulosic liquid media consisted of M9 salt solution to which strips of filter paper or newspaper had been added. Alternatively, Avicell (powder) was added to 0.1% (w/v).

All bacteriologic assays and growth procedures were performed using standard bacteriology techniques, methods and medias. Non-fermentative analysis was performed using an API non-fermentor identification system. MIDI analysis was performed using standard protocols. ATCC 55703 and ATCC 55702 were found to grow aerobically on a wide variety of solid and soluble cellulosic materials. ATCC 55703 and ATCC 55702 grew in complex medium under reducing conditions and weakly on complex media under full anaerobic conditions. No anaerobic growth was observed in liquid cellulosic medium. Standard bacteriologic identification methods and assimilation studies suggested that these two bacteria have few characteristics corresponding to the genus/species *P. fluorescens*. Assimilation studies suggested only a low probability match with the genus Sphingomonas.

Metabolic and physical characterization of ATCC 55703 and ATCC 55702 revealed that they were alkalophilic, non-fermentative, gram negative, oxidase positive, motile, cellulose degrading bacteria. The aerobic substrate utilization profile of these bacteria were found to have few characteristics consistent with a classification of *P. fluorescens* with a very low probability match with the genus Sphingomonas. ATCC 55703 and ATCC 55702 were found to grow best aerobically but also grew well in complex media under reducing conditions. ATCC 55703 and ATCC 55702 grew slowly under full anaerobic conditions on complex media and did not grow anaerobically on media in which cellulose was the sole carbon source. Total fatty acid analysis (MIDI) of ATCC 55703 and ATCC 55702 failed to group these bacteria with any known genus or species, although there was a very low probability match with the genus Vibrio.

Growth studies and non-fermentative analysis indicate that ATCC 55703 and ATCC 55702 are small, non-fermentative, gram negative rod-shaped bacteria with few characteristics that are typically associated with *P. fluorescens* or even with the genus Pseudomonas. Specifically, Table 1, below, illustrates the similarities and differences between ATCC 55703 and ATCC 55702 with respect to *P. fluorescens* regarding standard biochemical assays.

TABLE 1

| Test | P. fluorescens | ATCC 55703 and ATCC 55702 |
| --- | --- | --- |
| Growth on Blood Agar | + | − |
| Growth on MacConkey's Agar | + | − |
| Growth in Pseudomonas M10 Medium | + | − |
| Catalase | Strong Positive | Weak Positive |
| Growth in Thioglycollate | Aerobic | Anaerobic |
| Fluorescence | + | − |
| Oxidase | + | + |
| Tryptophanase | − | − |
| Arginine dihydrolase | + | − |
| Urease | − | − |
| Esculine | − | + |
| Gelatinase | + | − |
| PNGP | − | + |
| Glucose | + | + |
| Arabinose | + | + |

TABLE 1-continued

| Test | P. fluorescens | ATCC 55703 and ATCC 55702 |
| --- | --- | --- |
| Mannose | + | − |
| n-Acetyl-Glucosamine | + | + |
| Maltose | − | + |
| Gluconate | + | − |
| Caprate | + | − |
| Adipate | + | − |
| Malate | + | − |
| Phenylacetate | ± | − |

Table 2, below, illustrates various morphological and biochemical characteristics of both ATCC 5573 and ATCC 55702.

TABLE 2

| | |
| --- | --- |
| Gram Morphology | Small gram negative rod approximately 0.5 μm |
| Motility | Motile at 25 and 37° C. |
| Starch Hydrolysis (amylase) | Positive for starch hydrolysis |
| β-galactosidase | Positive |
| β-glucosidase | Positive |
| Hemicellulase | Positive |
| Xylanase | Positive |
| Optimal Growth Temperature (complex media) | 30–37° C. |
| Optical pH (complex media) | pH 7.2–8.0 |
| Anaerobic growth (37° C.) | |
| Blood Agar | Positive |
| Trypticase Soy Broth | Positive |
| CMC Liquid Medium | Negative |
| CMC Solid Medium | Negative |
| Avicel Liquid Medium | Negative |
| Filter Paper Liquid Medium | Negative |
| Aerobic Growth on Cellulosic Media* | |
| CMC | Positive (solid and liquid) |
| Avicel | Positive (solid and liquid) |
| Filter paper | Positive (solid) |
| Cellobiose | Positive (solid) |
| Newspaper | Positive (liquid) |
| Cellulose acetate | Positive (liquid) |
| Nitrocellulose | Negative (liquid) |
| Polyacrylamide | Negative (liquid) |
| Growth on Other Media (by ATCC 55702 only) | |
| Media | Growth by ATCC 55702 |
| 20% v/v Furfurol | Positive |
| 20% v/v Cinnimyl Alcohol | Positive |
| 20% v/v Saccharinic Acid | Positive |

*Standing or shake culture at 30 or 37° C.

ATCC 55703 and ATCC 55702 can utilize a wide variety of solid and soluble cellulosic media as a sole carbon source which is consistent with previous observations. ATCC 55703 and ATCC 55702 are oxidase and catalase positive, motile, and aerobic, which are the few characteristics that suggest it might be related to the Pseudomonads. ATCC 55703 and ATCC 55702 only weakly clot a lymulus lysate test, which is interesting because gram staining indicates that they are 0.5–1 μm gram negative rods.

Table 3, below, illustrates additional biochemical characteristics of ATCC 55703:

| | |
| --- | --- |
| Indole Production | Negative |
| N-acetyl glucosaminidase | Positive |

| | |
|---|---|
| α-Glucosidase | Positive |
| α-Arabinosidase | Positive |
| β-Glucosidase | Positive |
| α-Fucosidase | Negative |
| Phosphatase | Negative |
| α-Galactosidase | Positive |
| β-Galactosidase | Negative on An-Ident* |
| Indoxyl-acetate hydrolysis | Positive |
| Arginine Utilization | Negative |
| Leucine aminopeptidase | Positive |
| Proline aminopeptidase | Positive |
| Pyroglutamic acid arylamidase | Negative |
| Tyrosine aminopeptidase | Negative |
| Arginine aminopeptidase | Positive |
| Alanine aminopeptidase | Positive |
| Histidine aminopeptidase | Positive (weak) |
| Phenylalanine aminopeptidase | Positive |
| Glycine aminopeptidase | Positive |

*Colonies of ATCC 55703 and ATCC 55702 are positive for β-galactosidase after incubation with X-gal The ablility of cultures of ATCC 55703 and ATCC 55702 to grow at various temperatures was evaluated by measuring the aborbance of the cultures at 600 nm as a function of time. ATCC 55703 and ATCC 55702 have an operative temperature range of 5–37° C., a preferred temperature range of 25–32° C., and an optimal temperature of 30° C. No growth of ATCC 55703 or ATCC 55702 has been observed at 45° C. With respect to the cellulase produced by ATCC 55703 and ATCC 55702, the operating temperature range is 5–70° C. (at pH 7.5). The preferred temperature is 55° C. (at pH 7.5).

The tolerance of ATCC 55703 and ATCC 55702 for extremes of pH was evaluated by determining the reduction in colony forming units as a function of the length of exposure of bacteria to extremes of pH. Bacteria were exposed to various pH conditions, appropriate dilutions were plated at different time intervals, and the number of colonies formed were counted. Both ATCC 55702 and 55703 have an operating pH range of 6.8 to 9.0, a preferred pH range of 7.2 to 8.0, with growth decreasing after the pH is adjusted below pH 7.0. In complex media, ATCC 55703 and ATCC 55702 reduced the medium pH below pH 6.8, whereas in liquid cellulosic medium the pH does not fall more than 0.3 pH units from the starting pH of 7.2. The cellulase produced by ATCC 55703 and ATCC 55702 has an operating pH range of 5–11 (at 55° C.). The preferred pH range is 7–8 (at 55° C.).

The salt tolerance of ATCC 55703 and 55702 was determined by growing bacteria in cultures containing various salt concentrations and measuring the absorbance at 600 nm as a function of time. ATCC 55703 and ATCC 55702 have a relatively high salt tolerance, with an operating salt range of 8.5–32 mM sodium, with a preference of 8.5 mM sodium. As a consequence, less dilution of high salt brines used in paper processing will be required to use ATCC 55703 and ATCC 55702 in the biodegradation of cellulosic waste from the paper industry.

Taxonomic characterization of ATCC 55703 and ATCC 55702 using total fatty acid analysis failed to group these bacteria with any of the currently recognized genera. Since the non-fermentative analysis suggested that ATCC 55703 and ATCC 55702 may be distantly related members of the genus Sphingomonas, a total lipid analysis was also performed on ATCC 55703 and ATCC 55702. The lipid profiles of ATCC 55703 and ATCC 55702 are unremarkable. Results indicated that no sphingolipid is produced by ATCC 55703 or ATCC 55702 and the predominant phospholipids are acyl-linked glycerophosphatides.

Total fatty acid profiling has been used to identify anaerobic and aerobic bacteria. Total fatty acid analysis failed to adequately group ATCC 55703 or ATCC 55702 into any known genus. Only a low probability match with the genus Vibrio was obtained. Total fatty acid analysis found that a large percentage of the fatty acids produced by ATCC 55703 and ATCC 55702 are in the trans configurations which is characteristic of some members of Vibrio. Ribosomal phylogenetic analysis will probably more closely define the taxonomic position of these bacteria.

Evaluation of Cellulase Production

The relative amount of extracellular cellulase produced by ATCC 55702 and 55703 was determined as follows. Uniform amounts of the bacteria in a small volume were applied to 0.1% carboxymethyl cellulose (CMC) medium and allowed to grow for various lengths of time. The cellulose in the media was visualized by first staining with Congo Red dye and then destaining with 1M NaCl. Clear zones that were not stained by the dye occured about bacterial colonies producing extracellular cellulase. The zone size is positively correlated with the amount of cellulase produced. ATCC 55702 was associated with a much larger clear zone than was ATCC 55703, indicating that ATCC 55702 produces greater amounts of extracellular cellulase.

Bacterial isolate ATCC 55702 was compared with 11 other cellulose-degrading bacteria isolated from termite gut. The results, summarized in Table 5, demonstrate that ATCC 55702 is superior in (1) production of cellulase, (2) degradation of solid cellulose, and (3) conversation of solid cellulase to sugars when compared to 11 other cellulose degrading bacteria isolated from termite gut.

TABLE 4

| Species | Filter Paper Degradation (Days)* | Extracellular Cellulase (mm) (Day 5)** | Total Carbohydrate (μg/ml)**** |
|---|---|---|---|
| ATCC 55702 | 3 | 12 | 36.5 |
| Species 1*** | >7 | 0 | 0 |
| Species 2 | >7 | 0 | 0 |
| Species 3 | >7 | 0 | 0 |
| Species 4 | 4 | 0 | 18.1 |
| Species 5 | >7 | 0 | 0 |
| Species 6 | >7 | 0 | 0 |
| Species 7 | >7 | 0 | 0 |
| Species 8 | 6 | 0 | 0 |
| Species 9 | >8 | 0 | 0 |
| Species 10 | >8 | 0 | 0 |
| Species 11 | 6 | 0 | 0 |

*First appearance of filter paper structure is degrading
**Plate diffusion assay zone based on CMC hydrolysis
***Strains isolated from termite gut and include Bacillus sp., Pseudomonas Sp., and Flavobacterium Sp.-like
****Total carbohydrate in culture supernatants after 5 days growth on newspaper It has also been found that for ATCC 55702 to grow rapidly on solid cellulose and produce the highest amounts of extracellular endocellulase, it must produce high levels of β-glucosidase (cellobiase) activity. This enzyme converts cellobiose to glucose. ATCC 55702 rapidly produces a colored product from X-GLU (a synthetic marker/text for β-glucosidase production). Therefore, ATCC 55702 is enhanced not only in the production of extracellular cellulases (endoglucanases), but is also enhanced for β-glucosidase activity.

Sensitivity of ATCC 55702 and ATCC 55703 to Ultraviolet Radiation.

Introduction of new genetic traits into bacteria are inhibited by the enzymes which repair the genetic material (DNA repair and recombination). Thus, any trait introduced into a bacterium by either classical methods (mutagenesis) or recombinant DNA technologies (genetic engineering) can be destroyed by rearrangement of the genetic material by host enzymes, such as recombinase. In the most commonly used bacterial cloning system, *Escherichia coli*, recombinase deficient (rec−) cloning hosts have been created that lack these recombinase genes. However, cloning of cellulase genes into *E. coli* is not commercially practical since the organism cannot secrete the cellulase. Consequently, genetic enhancement of a bacteria that already produces cellulasea using standard and recombinant DNA technologies is highly desirable.

The sensitivity of ATCC 55702 and ATCC 55703 to ultraviolet (UV) radiation was compared with that of a rec− strain of *E. coli*. Using standard methods, a known number of each of the bacterial strains were exposed to UV radiation for from 0–100 s. Appropriate dilutions of the bacteria were plated on suitable media, the bacteria were allowed to grow, and the numbers of colonies were determined. ATCC strain 55702 was found to have a sensitivity to UV radiation that is comparable to that of the *E. coli* rec− strain, whereas ATCC strain 55703 is relatively insensitive to UV radiation. ATCC 55702 is therefore be an improved host for genetic manipulations using recombinant DNA techniques, and is less likely to destroy genetic mutations obtained through standard mutagenesis techniques.

Differentiation between transformed and untransformed cells is commonly achieved by selection on medium containing an antibiotic for which the vector carriers a resistance marker. Therefore, ideal cloning hosts are generally sensitive to tetracycline and ampicillin, antibiotics that are commonly used to select for transformants. Antibiotic sensitivity testing of ATCC 55703 revealed that this strain is resistant to ampicillin and partially resistant to tetracycline. The results of antibiotic sensitivity testing of ATCC 55702 is summarized in Table 5, below:

TABLE 5

| Antibiotic | μg/ml conc. | 50 μg/ml conc. | 100 μg/ml conc. | 200 μg/ml conc. |
| --- | --- | --- | --- | --- |
| Streptomycin | s* | s | s | s |
| Tetracycline | r | s | s | s |
| Chloramphenicol | s | s | s | s |
| Ampicillin | r | r | s | s |
| Penicillin G | r | r | r | r |
| Gentamicin | s | s | s | s |

*s = sensitive, r = resistant

As previously mentioned, ATCC 55703 was subjected to an intensive mutagenesis regimen using MNNG. Resulting strains were subjected to replica plating for selection of: (1) improved soluble cellulase production; (2) rapid degradation of solid cellulose and waste products (filter paper, newsprint and diapers); (3) UV sensitivity; (4) enhanced β-glucosidase activity; (5) tetracycline and ampicillin sensitivity; and (6) high levels of total carbohydrate production from solid cellulose. As a result of replica plating procedures, ATCC 55702 was identified.

Construction of a Recombinant Vector Having a Cellobiase Gene.

A recombinant vector comprising a heterologous cellulase gene operably connected to a promoter was constructed as follows. A gene encoding a 23 kd cellulase from *Pseudomonas cellulosa* (Wolff, et al. *J. Indus. Microbiol.* 6:285–290, 1990) was obtained from Dr. Bernard Glick, contained within a 10.6 kb insert in pPFC4. The entire coding sequence of the cellulase gene is contained within approximately 600 to 1000 base pairs near the 5' end of the insert. Digestion of pFC4 by PvuII generates 4 fragments, including a 3 kb fragment containing the cellulase gene. The 3 kb PvuII fragment was digested with BamHI to obtain a 1.4 kb fragment containing the cellulase gene. The 1.4 kb PvuII-BamHI fragment was ligated to pUC19 DNA that had been linearized with SmaI and BamHI. The ligation mix was used to transform Epicurean Coil SURE (Stratgene, Inc.), a commercial *E. Coli* host strain. Purified plasmid DNA was obtained from large scale preparations of a transformant containing the cellulase gene, using standard molecular biological techniques. The 1.4 kb insert was removed from pUC19 by digestion with EcoRI and HindIII, and ligated to EcoRI- and HindIII-digested pMMB66EH and pMMB67EH DNA. These plasmids, which are identical except for the orientation of the multiple cloning region, were obtained from Dr. Gary Sailor, University of Tennessee, Knoxville.

Transformation of ATCC 55702

ATCC 55702 was transformed with the recombinant vector containing the cellulase gene by means of electroporation, using standard methods.

Selection and Screening of Transformants

Transformants were selected on CMC agar plates containing ampicillin (100 ug/ml). To confirm that ampicillin resistant colonies contained the recombinant plasmid, small-scale preparations of plasmid DNA were made using standard methods known to one skilled in the art. The plasmid DNA was digested with EcoRI and BamHI, and the sizes of fragments thus obtained were determined by agarose gel electrophoresis. The profile of fragment sizes indicated that the ampicillin resistant colonies did contain the recombinant plasmid. Mutagenesis of transformants Transformants were mutagenized by treatment with MNNG (J. H. Miller, *A short course in bacterial genetics* p 293–297, Cold Spring Harbor Press, 1992). The vector employed in the construction of the recombinant vector is a low copy number plasmid (1–3 plasmids/bacterium) that is rop+, meaning that the vector contains the sequences necessary for regulation of plasmid replication and partioning. The transformants were mutagenized with the hope that mutagenesis would interfer with regulation of plasmid copy number and cause an increase plasmid copy number, and thereby enhance cellulase production.

Evaluation of Cellulase Production by Transformants.

The relative amounts of extracellular cellulase produced by untransformed ATCC 55702 and mutagenized transformants of ATCC 55702 comprising a recombinant vector with a cellulase gene were examined by comparing the relative sizes of the clear zones surrounding bacterial colonies plated on Congo red-stained CMC plates. The zone sizes of mutagenized transformants containing the recombinant vector with the cellulase gene were several times larger than the zone sizes of untransformed ATCC 55702. Following a 24-h incubation, the zone sizes were measured. Several of the mutagenized transformants had zone sizes that were much larger (11 mm) than the zone formed about untransformed ATCC 55702 (4 mm). It is estimated that cellulase production is from about 3 to 10 times greater in transformants than in nontransformants. This is most likely due to a gene dosage effect resulting from the introduction of the cellulase gene into the bacteria. Although plasmid copy number was not determined for the mutagenized transformants, it is likely that mutagenesis did not increase the plasmid copy number as hoped. Had there been an increase in plasmid copy number, one would expect that cellulase production would have been enhanced to a greater extent.

In accordance with one aspect of the present invention, a simple powder containing the cellulase and bacteria can be used as an additive to cellulosic waste (i.e., diapers, tampons, newsprint, etc.). The product would be embodied as an inexpensive dried or lyophilized powder of the total fermentate which contains bacteria and cellulase. No post fermentation ("down stream") processing would be required. The product would only require fermentation, lyophilization or drying, and packaging. The powder could consist alternatively of: (1) dried fermentate (cellulase) plus cells (bacteria); (2) dried cells (bacteria) ; or (3) dried fermentate (cellulase). Additionally, the product could be packaged in a liquid format. Thus, the liquid product could consist alternatively of: (1) fermentate (cellulase); (2) lysed cells (bacteria); or (3) fermentate (cellulase) plus lysed cells (bacteria).

I claim:

1. A transformant of a bacterium having all of the identifying characteristics of *Pseudomonas cellulosa* ATCC 55702, the transformant comprising a recombinant vector having a heterologous cellulase gene operably connected to a promoter and a selectable marker, wherein the transformant exhibits a higher level of cellulase activity than the untransformed bacterium.

2. The bacterial transformant of claim 1, wherein the transformant is *Pseudomonas cellulosa* ATCC 202032.

3. A method of degrading cellulosic material comprising contacting the cellulosic material with an effective amount of the cellulase produced by a transformant of a bacterium, the bacterium having all of the identifying characteristics of ATCC 55702, the transformant comprising a recombinant vector having a heterologous cellulase gene operably connected to a promoter and a selectable marker, and wherein the transformant exhibits a higher level of cellulase activity than the untransformed bacterium.

4. The method of claim 3, wherein the transformant is *Pseudomonas cellulosa* ATCC 202032.

5. The transformant of claim 1, wherein the transformant has been mutagenized to further enhance cellulase production relative to the unmutagenized transformant.

* * * * *